United States Patent
Yuan et al.

(10) Patent No.: US 11,390,893 B2
(45) Date of Patent: Jul. 19, 2022

(54) METHOD FOR EXTRACTING COENZYME Q10 AND PHOSPHOLIPID FROM COENZYME Q10 FERMENTATION BACTERIAL POWDER

(71) Applicants: ZHEJIANG NHU COMPANY LTD., Zhejiang (CN); ZHEJIANG UNIVERSITY, Zhejiang (CN); HEILONGJIANG NHU BIOTECHNOLOGY COMPANY LTD., Hei Longjiang (CN); SHANGYU NHU BIOLOGICAL CHEMICAL CO., LTD., Zhejiang (CN)

(72) Inventors: Shenfeng Yuan, Zhejiang (CN); Yang Yao, Zhejiang (CN); Yi Min, Zhejiang (CN); Baishan Hu, Zhejiang (CN); Zhaofeng Chen, Zhejiang (CN); Yong Li, Zhejiang (CN); Qichuan Li, Zhejiang (CN); Yunxuan Luo, Zhejiang (CN); Jinyang Zhang, Zhejiang (CN); Xuguang Li, Zhejiang (CN); Shichun Tu, Zhejiang (CN)

(73) Assignees: ZHEJIANG NHU CO. LTD., Zhejiang (CN); ZHEJIANG UNIVERSITY, Zhejiang (CN); HEILONGJIANG NHU BIOTECHNOLOGY CO. LTD., Hei Longjiang (CN); SHANGYU NHU BIOLOGICAL CHEMICAL CO., LTD., Zhejiang (CN)

( * ) Notice: Subject to any disclaimer, the term of this patent is extended or adjusted under 35 U.S.C. 154(b) by 0 days.

(21) Appl. No.: 16/957,797

(22) PCT Filed: May 23, 2018

(86) PCT No.: PCT/CN2018/088045
§ 371 (c)(1),
(2) Date: Jun. 25, 2020

(87) PCT Pub. No.: WO2019/128060
PCT Pub. Date: Jul. 4, 2019

(65) Prior Publication Data
US 2020/0399667 A1   Dec. 24, 2020

(30) Foreign Application Priority Data
Dec. 25, 2017  (CN) .......................... 201711422709.0

(51) Int. Cl.
*C12P 7/66* (2006.01)
*C07C 46/10* (2006.01)

(52) U.S. Cl.
CPC ................ *C12P 7/66* (2013.01); *C07C 46/10* (2013.01)

(58) Field of Classification Search
None
See application file for complete search history.

(56) References Cited

U.S. PATENT DOCUMENTS

2020/0399667 A1\* 12/2020 Yuan ......................... C12P 7/66

FOREIGN PATENT DOCUMENTS

| CN | 102876743 A | 1/2013 |
| CN | 103238833 A | 8/2013 |

(Continued)

OTHER PUBLICATIONS

Park et al., "Fatty acids of extractable and bound lipids of Rhodomicrobium vannielii", Journal of Bacteriology, vol. 93, No. 1, pp. 230-236, 1967 (Year: 1967).\*

(Continued)

*Primary Examiner* — Richard C Ekstrom
(74) *Attorney, Agent, or Firm* — Young Basile Hanlon & MacFarlane, P.C.

(57) ABSTRACT

The present application relates to a method for extracting coenzyme Q10 and a phospholipid from a coenzyme Q10 fermentation bacterium powder. The method is characterized in that the fermentation bacterium powder of a coenzyme Q10 production strain is subjected to extraction with a mixed solvent of which the three-dimensional Hansen solubility parameter is between 21 and 23 $(J/cm^3)^{1/2}$ and the (Continued)

hydrogen bonding solubility parameter thereof is between 10 and 12 $(J/cm^3)^{1/2}$. The present invention can efficiently extract two products, namely coenzyme Q10 and a phospholipid, from the coenzyme Q10 fermentation bacterium powder; the process thereof is highly operable, easy to be industrialized, and can provide a product with high purity and yield, having great economic benefit.

20 Claims, 2 Drawing Sheets

(56) References Cited

FOREIGN PATENT DOCUMENTS

| | | |
|---|---|---|
| CN | 104099395 A | 10/2014 |
| CN | 104323283 A | 2/2015 |
| CN | 105420417 A | 3/2016 |

OTHER PUBLICATIONS

Carr et al., "Ubiquinone concentrations in Arthiorhodaceae grown under various environmental conditions", Biochemical Journal, vol. 96, pp. 688-692, 1965 (Year: 1965).*

Thesis for Masters Degree Northwest A & F University in 2007, Studies on Screening and Fermentation Conditions of Coenzyme Q10 Overproductive Mutant; Name of Postgraduate: Li Ju-hai, Adviser: Prof. Yue Tian-li, Date of submission: May 2007, Yangling Shaanxi China; Classification code: TS20 1.3, UDC: 577. 161.6; University code: 10712; Postgraduate No. SY20040450, 102 pages.

* cited by examiner

METHOD FOR EXTRACTING COENZYME Q10 AND PHOSPHOLIPID FROM COENZYME Q10 FERMENTATION BACTERIAL POWDER

TECHNICAL FIELD AND PRIORITY

This application is a National Stage Entry under 35 U.S.C. 371 of PCT/CN2018/088045 which claims priority from CN 201711422709.0 filed Dec. 25, 2017. The entire contents of these applications are incorporated herein by reference in their entirety The present disclosure relates to the technical field of biological extraction, and particularly relates to a method for extracting coenzyme Q10 and a phospholipid from coenzyme Q10 fermentation bacterium powder.

BACKGROUND

Coenzyme Q10 is widely used in the fields of biomedicine, cosmetics and health-care products, and has the functions of enhancing human immunity, anti-tumor, anti-oxidation, protecting heart and brain, improving microcirculation, promoting learning and memory, improving exercise capacity, etc. And the molecular formula thereof is as follows.

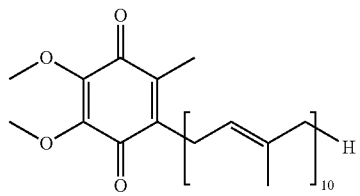

The methods for preparing coenzyme Q10 mainly include animal cell extraction, tobacco solanesol semi-synthesis, complete synthesis, microbial fermentation, plant cell culture, etc. Among them, the microbial fermentation extraction is a main production mode. As for the extraction method of coenzyme Q10, the conventional method is an organic solvent extraction method, and in recent years, an ultrasonic-assisted method, a supercritical carbon dioxide extraction method, a subcritical fluid extraction method, and the like have been developed.

Chinese patent CN101314782A discloses a method for extracting coenzyme Q10 from bacteria, which comprises the steps of carrying out reflux extraction for 5 to 60 minutes with chloroform, acetone, carbon tetrachloride, petroleum ether and/or the like as a solvent; evaporating the solvent of the extract to dryness; thereafter, dissolving the extract by using diethyl ether or petroleum ether; and then carrying out silica gel column chromatography purification to obtain coenzyme Q10.

Chinese patent CN102557912A discloses a method for saponifying coenzyme Q10 extract solution, which comprises the steps of firstly performing stirring with petroleum ether, pentane, n-hexane, heptane, octane or the like as a solvent at 10 to 50□ for 1 to 3 hours to extract from coenzyme Q10 bacteria for 2 to 4 times; and then saponifying the extract solution.

Chinese patent CN104529738A discloses a method for extracting coenzyme Q10 from bacteria, which comprises the steps of subjecting bacteria to wall breaking treatment and saponification process; extracting twice with petroleum ether as a solvent; evaporating the solvent; and then performing purification to obtain coenzyme Q10.

Chinese patent CN104694613A discloses a method for extracting coenzyme Q10 from bacteria, which comprises the steps of firstly extracting with n-hexane as a solvent; then performing saponification; and lastly obtaining coenzyme Q10 through silica gel column chromatography, recrystallization and other steps.

Chinese patent CN106146278A discloses a method for extracting coenzyme Q10 from bacterial residues, which comprises the steps of carrying out percolation extraction with n-hexane, ethyl acetate, n-heptane, petroleum ether, acetone or the like as a solvent; concentrating the percolation solution to obtain a solid crude product; thereafter, dissolving the solid crude product in any one of n-hexane, n-heptane and petroleum ether; and then removing impurities through multi-stage extraction to obtain coenzyme Q10.

Chinese patent CN101381747A discloses an ultrasonic-assisted extraction method of coenzyme Q10, which comprises the steps of carrying out ultrasonication at 0□ with water, acetone, chloroform, n-hexane, diethyl ether, methanol, ethanol or petroleum ether as a solvent, wherein the ultrasonic frequency is 0.2 to 0.8 and the power is 300 to 500 W; and then performing separation to obtain coenzyme Q10.

Chinese patent CN103819326A discloses an ultrasonic-assisted extraction method of coenzyme Q10, which comprises the steps of firstly ultrasonic disruption bacteria in a hydrochloric acid solution, wherein the ultrasonic frequency is 0.3 to 0.8 and the power is 200 to 800 W; adjusting the pH value to 5 to 9; then extracting twice with at least one of methanol, ethanol, ethylene glycol, isopropanol, n-butanol, ethyl acetate, petroleum ether and trichloromethane as a solvent, and each extraction was carried out with stirring for 2 to 3 hours, wherein the extraction temperature is 20 to 80□; and then carrying out chromatography and crystallization to obtain coenzyme Q10.

Chinese patent CN102391092A discloses a method for extracting coenzyme Q10 from bacteria by using supercritical carbon dioxide, wherein the extraction conditions are as follows: pressure: 24.5 MPa, temperature: 35□, extraction time: 45 minutes; and the extract liquor is subjected to alkali treatment, silica gel column chromatography, etc. to obtain coenzyme Q10.

Chinese patent CN104591993A discloses a method for extracting coenzyme Q10 from bacteria by using subcritical propane, butane, dimethyl ether and/or the like, wherein the extraction conditions are as follows: pressure: 0.2 to 1.0 MPa, temperature: 10 to 60□, extraction time: 10 to 60 minutes; and then the extract is subjected to a subsequent purification treatment to obtain coenzyme Q10.

The above methods extract only one active ingredient, namely coenzyme Q10, from a coenzyme Q10 fermentation bacterium powder. Other active ingredients in the bacterium powder, such as phospholipids, are discarded in the form of bacterial residues or are damaged in the saponification process, resulting in waste of phospholipids.

Phospholipids, which are phosphate group-containing lipids, are a basic substance of life. The molecular formulas of several common phospholipids are as follows:

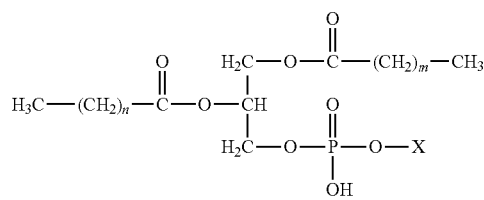

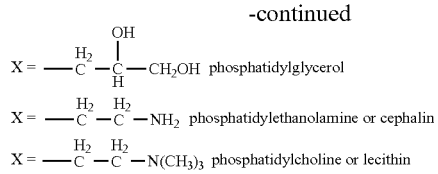

Phospholipids play an important role in activating cells; maintaining metabolism, basal metabolism and balanced secretion of hormones; and enhancing immunity and regenerative capacity of human bodies. In addition, phospholipids also have effects of promoting fat metabolism, preventing fatty liver, reducing serum cholesterol, improving blood circulation, and preventing cardiovascular diseases. Phospholipids can decompose excessively high blood fat and excessively high cholesterol, and clean blood vessels to ensure smooth circulation in blood vessels, so they are recognized as "vascular scavengers". In the United States, the total sales of lecithin health-care products rank third only after those of multivitamins and vitamin E. In the food industry, phospholipids are often used as emulsifiers to allow oils to disperse in water.

In a coenzyme Q10 fermentation bacterium powder, the content of phospholipid is 10% or more, which is more than 3 times the content of coenzyme Q10. However, coenzyme Q10 and a phospholipid are quite different in terms of molecular structure, so technically, it is extremely difficult to efficiently extract both coenzyme Q10 and a phospholipid from a coenzyme Q10 fermentation bacterium powder. Moreover, there are few reports in the prior art about the technology for extracting a phospholipid from a coenzyme Q10 fermentation powder.

SUMMARY

Problems to be Solved by this Disclosure

The present disclosure aims to solve the problem in the prior art that only coenzyme Q10 is extracted from a coenzyme Q10 fermentation powder while a large amount of the phospholipid ingredient is treated as bacterial residues, and provides a method for extracting coenzyme Q10 and a phospholipid from a coenzyme Q10 fermentation bacterium powder

Means for Solving the Problem

The present disclosure relates to a method for extracting coenzyme Q10 and a phospholipid from a coenzyme Q10 fermentation bacterium powder, wherein a fermentation bacterium powder of a coenzyme Q10 production strain is subjected to extraction with a mixed solvent of which a three-dimensional Hansen solubility parameter is between 21 and 23 $(J/cm^3)^{1/2}$ and a hydrogen bonding solubility parameter thereof is between 10 and 12 $(J/cm^3)^{1/2}$.

In the above method, the mixed solvent is a mixed solvent formed by a solvent (a) and a solvent (b), the solvent (a) is at least one of tetrahydrofuran, ethyl acetate, diethyl ether, butanone, dichloromethane, chloroform, n-pentane, n-hexane, n-heptane and cyclohexane, and the solvent (b) is at least one of methanol, ethanol, n-propanol and isopropanol.

In the above method, the mixed solvent is preferably tetrahydrofuran-methanol, ethyl acetate-methanol, ethyl acetate-ethanol, chloroform-methanol, chloroform-ethanol, n-hexane-methanol, n-hexane-ethanol, or n-hexane-n-propanol.

In the above method, a using amount of the mixed solvent is 3 to 10 times the weight of the coenzyme Q10 fermentation bacterium powder; and preferably, the temperature of the extraction is 10 to 60□, and the extraction is carried out 2 to 5 times.

In the above method, the extraction is one of immersion extraction, percolation extraction, reflux extraction, decoction extraction and ultrasonic-assisted extraction; and preferably, the extraction is the immersion extraction.

In the above method, an extraction liquor obtained after carrying out the extraction is subjected to separation by the following method, in said method, 1) the extraction liquor is concentrated to dryness, the resultant is dissolved with a low-polarity solvent, filtered to remove insoluble substances, concentrated again to a weight which is 30% to 90% of the weight of the coenzyme Q10 fermentation bacterium powder, and then added into acetone; after being completely mixed and dissolved, the resultant is subjected to cooling and crystallization, and filtered to obtain a filter cake and a filtrate; the filter cake is washed with acetone, and a phospholipid is obtained after drying; and 2) the filtrate and a washing liquid obtained in step 1) are combined, the resultant is concentrated to dryness, n-hexane is added thereto for dissolving, and then the resultant is washed with a lower alcohol aqueous solution; and the solution obtained after washing is concentrated to dryness, ethanol is added thereto for dissolving, and then the resultant is subjected to cooling and crystallization to obtain a coenzyme Q10 crude product.

In the above method, the low-polarity solvent in the step 1) is one of pentane, hexane and petroleum ether; and preferably, a using amount of the low-polarity solvent is 1 to 5 times the weight of the coenzyme Q10 fermentation bacterium powder.

In the above method, the using amount of acetone used in the step 1) is 2 to 8 times the weight of the coenzyme Q10 fermentation bacterium powder; and the using amount of n-hexane used in step 2) is 0.5 to 4 times the weight of the coenzyme Q10 fermentation bacterium powder.

In the above method, the lower alcohol aqueous solution in the step 2) is one of methanol aqueous solution, ethanol aqueous solution and isopropanol aqueous solution; preferably, the lower alcohol therein has a mass percentage of 50% to 95%; and preferably, a using amount of the lower alcohol aqueous solution is 1 to 8 times the weight of the coenzyme Q10 fermentation bacterium powder.

In the above method, a temperature for the crystallization in the step 2) is 0 to 20□, and preferably, the using amount of ethanol is 0.2 to 0.8 times the weight of the coenzyme Q10 fermentation bacterium powder.

In the above method, in the step 2), a decolorizing agent is added before crystallization to perform a decolorizing treatment; and preferably, the decolorizing agent is one of activated carbon, white clay and adsorbent resin.

In the above method, the coenzyme Q10 crude product obtained in the step 2) is subjected to silica gel column chromatography to obtain a high-purity coenzyme Q10.

Advantageous Effects

The present disclosure can efficiently extract two products, namely coenzyme Q10 and a phospholipid, from the coenzyme Q10 fermentation bacterium powder; the process thereof is highly operable, easy to be industrialized, and can provide a product with high purity and yield, having great economic benefit.

BRIEF DESCRIPTION OF THE DRAWINGS

The various features, advantages and other uses of the present apparatus will become more apparent by referring to the following detailed description and drawing in which.

DETAILED DESCRIPTION

Figure 1:
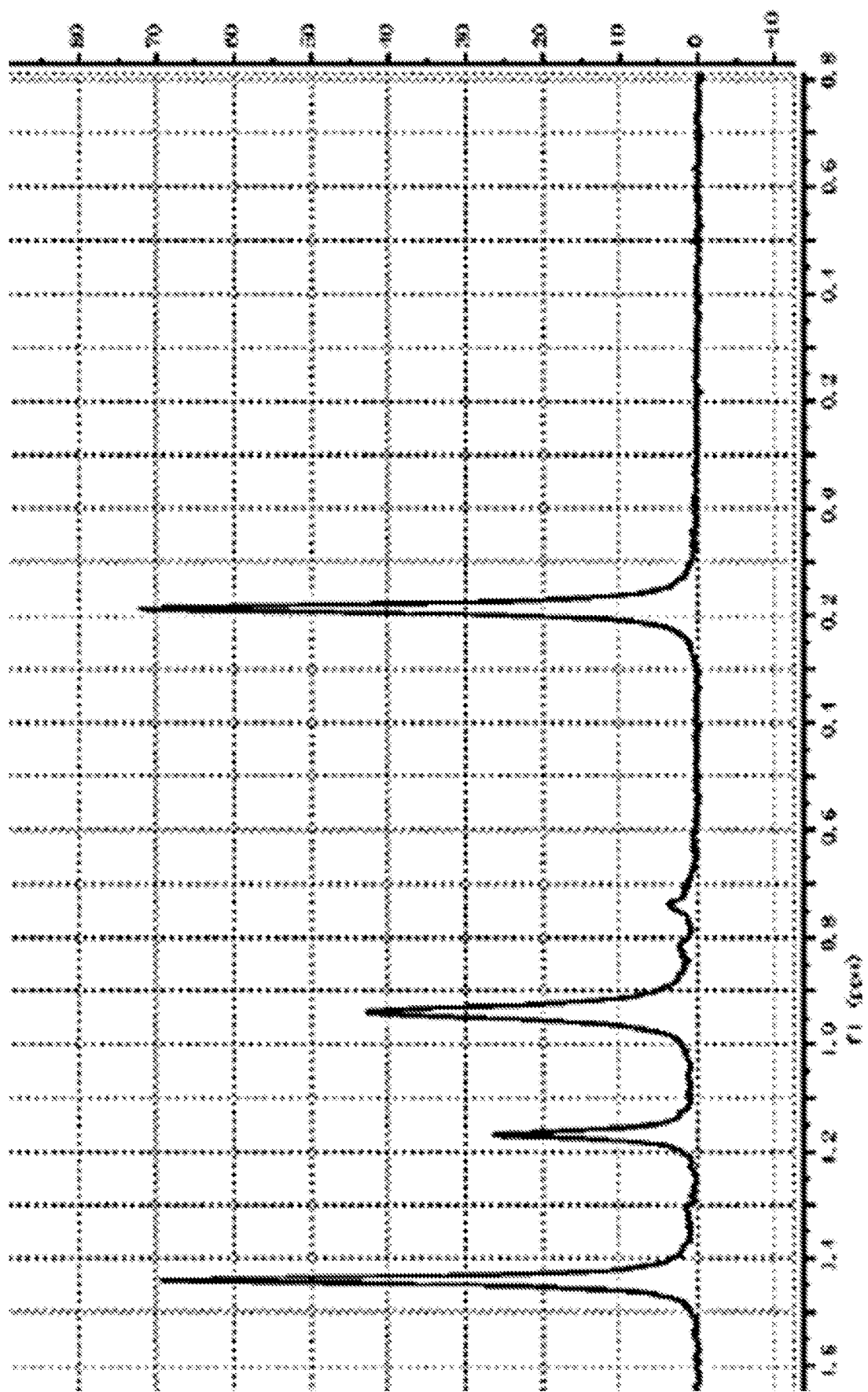
FIG. 1 shows a $^{31}$P NMR spectrum of the phospholipid obtained in Example 1 as disclosed herein.

Studies have found that although coenzyme Q10 and a phospholipid are quite different in molecular structure, they both have a long carbon chain structure and a function group capable of forming a hydrogen bond. When the solvent used for extraction from the coenzyme Q10 fermentation bacterium powder has a three-dimensional Hansen solubility parameter of between 21 and 23 $(J/cm^3)^{1/2}$ and a hydrogen bonding solubility parameter thereof of between 10 and 12 $(J/cm^3)^{1/2}$, both coenzyme Q10 and a phospholipid can be efficiently extracted from the coenzyme Q10 fermentation bacterium powder.

The three-dimensional Hansen solubility parameters of common solvents are readily available in the literature (e.g., the reference book, Hansen Solubility Parameters A User's Handbook). However, almost none of single solvents has a three-dimensional Hansen solubility parameter and a hydrogen bonding solubility parameter thereof falling within the above ranges, so mixed solvents are required to be used. The solubility parameter of a mixed solvent has linear additivity and is calculated according to the following formula I:

$$\delta_{mix} = \sum_{i=1}^{n} \varphi_i \delta_i \qquad \text{Formula I}$$

Where $\delta_{mix}$ is the three-dimensional Hansen solubility parameter of the mixed solvent, $\varphi_i$ is the volume fraction of the $i_{th}$ component in the mixed solvent, and $\delta_i$ is the three-dimensional Hansen solubility parameter of the $i_{th}$ component in the mixed solvent The hydrogen bonding solubility parameter of the solubility parameter of the mixed solvent is calculated according to the following formula II:

$$\delta_{h,mix} = \sum_{i=1}^{n} \varphi_i \delta_{h,i} \qquad \text{Formula II}$$

Where $\delta_{h,\,mix}$ is the hydrogen bonding solubility parameter of the three-dimensional Hansen solubility parameter of the mixed solvent, $\varphi_i$ is the volume fraction of the $i_{th}$ component in the mixed solvent, and $\delta_{h,i}$ is the hydrogen bonding solubility parameter of the three-dimensional Hansen solubility parameter of the $i_{th}$ component in the mixed solvent.

The method for extracting coenzyme Q10 and a phospholipid from a coenzyme Q10 fermentation bacterium powder in the present disclosure comprises the following steps: subjecting the coenzyme Q10 fermentation bacterium powder to extraction with a mixed solvent of which the three-dimensional Hansen solubility parameter is between 21 and 23 $(J/cm^3)^{1/2}$ and the hydrogen bonding solubility parameter thereof is between 10 and 12 $(J/cm^3)^{1/2}$, and then separating the extraction liquor to obtain a phospholipid and coenzyme Q10.

The mixed solvent of which the three-dimensional Hansen solubility parameter is between 21 and 23 $(J/cm^3)^{1/2}$ and the hydrogen bonding solubility parameter thereof is between 10 and 12 $(J/cm^3)^{1/2}$ is formed by a solvent (a) and a solvent (b), wherein the solvent (a) is at least one of tetrahydrofuran, ethyl acetate, diethyl ether, butanone, dichloromethane, chloroform, n-pentane, n-hexane, n-heptane and cyclohexane, and the solvent (b) is at least one of methanol, ethanol, n-propanol and isopropanol.

Preferably, the combination of the mixed solvent of which the three-dimensional Hansen solubility parameter is between 21 and 23 $(J/cm^3)^{1/2}$ and the hydrogen bonding solubility parameter thereof is between 10 and 12 $(J/cm^3)^{1/2}$ is one of tetrahydrofuran-methanol, ethyl acetate-methanol, ethyl acetate-ethanol, chloroform-methanol, chloroform-ethanol, n-hexane-methanol, n-hexane-ethanol and n-hexane-n-propanol.

The using amount of the mixed solvent is 3 to 10 times the weight of the coenzyme Q10 fermentation bacterium powder.

There is no particular requirement for the extraction method. Preferably, the extraction may be one of immersion extraction, percolation extraction, reflux extraction, decoction extraction and ultrasonic-assisted extraction. More preferably, the extraction is immersion extraction.

The extraction operation may be carried out in a manner commonly used in the art as long as coenzyme Q10 and a phospholipid can be efficiently extracted. Wherein the extraction temperature is preferably 10 to 60□, and the extraction is preferably carried out 2 to 5 times.

In the present disclosure, by using a mixed solvent of which the three-dimensional Hansen solubility parameter is between 21 and 23 $(J/cm^3)^{1/2}$ and the hydrogen bonding solubility parameter thereof is between 10 and 12 $(J/cm^3)^{1/2}$ to extract the active ingredients in the coenzyme Q10 fermentation bacterium powder, the extraction efficiency of both coenzyme Q10 and phospholipid can be ensured, and highly efficient extraction of the two active ingredients, i.e., coenzyme Q10 and a phospholipid can be achieved.

The extraction liquor obtained from the above method for extraction coenzyme Q10 and a phospholipid from a coenzyme Q10 fermentation bacterium powder is separated by the following method, in said method, 1) the extraction liquor is concentrated to dryness, the resultant is dissolved with a low-polarity solvent, filtered to remove insoluble substances, concentrated again to a weight which is 30% to 90% of the weight of the coenzyme Q10 fermentation bacterium powder, and then added into acetone; after being completely mixed and dissolved, the resultant is subjected to cooling and crystallization, and filtered to obtain a filter cake and a filtrate; the filter cake is washed with acetone, and a phospholipid is obtained after drying; and 2) the filtrate and a washing liquid obtained in step 1) are combined, the resultant is concentrated to dryness, n-hexane is added thereto for dissolving, and then the resultant is washed with a lower alcohol aqueous solution; and the solution obtained after washing is concentrated to dryness, ethanol is added thereto for dissolving, and then the resultant is subjected to cooling and crystallization to obtain a coenzyme Q10 crude product.

In the step 1), the extract is concentrated, then the concentrate is dissolved with a low-polarity solvent, filtered to remove most of the high-polar impurities in the form of insoluble substances to increase the purity of both coenzyme Q10 and phospholipid in the extraction liquor. The low-polarity solvent is one of pentane (n-pentane, isopentane, neopentane and mixtures thereof), hexane (n-hexane, 2-methylpentane, 3-methylpentane, 2,3-dimethylbutane, 2,2-dimethylbutane and mixtures thereof) and petroleum ether, and the using amount of the low-polarity solvent is 1 to 5 times the weight of the coenzyme Q10 fermentation bacterium powder.

After the low-polarity solvent is concentrated in the step 1), by making use of the characteristics of the low solubility of phospholipids in acetone and the high solubility of coenzyme Q10 in acetone, it is very simple to separate phospholipids in the form of insoluble substances from the acetone solution, and therefore, a high-purity phospholipid product is obtained in a high yield. The using amount of the acetone is 2 to 8 times the weight of the coenzyme Q10 fermentation bacterium powder; and the n-hexane is used in the step 2) in an amount of 0.5 to 4 times the weight of the coenzyme Q10 fermentation bacterium powder.

In the step 2), after concentrating the acetone in the combined filtrate and washing liquid, n-hexane is added thereto for dissolving, and then the resultant is washed with lower alcohol aqueous solution to remove high-polar impurities to further improve the purity of coenzyme Q10 in the solution, and ensure the smooth progress of the subsequent crystallization process. The lower alcohol aqueous solution is one of methanol aqueous solution, ethanol aqueous solution and isopropanol aqueous solution, wherein the lower alcohol therein has a mass percentage of 50% to 95%, and the using amount of the lower alcohol aqueous solution is 1 to 8 times the weight of the coenzyme Q10 fermentation bacterium powder.

In the step 2), the temperature for the crystallization is 0 to 20□, and the using amount of the ethanol is 0.2 to 0.8 times the weight of the coenzyme Q10 fermentation bacterium powder.

In the step 2), before the crystallization, a decolorizing agent may be added to perform decolorization treatment. The decolorizing agent may be one of activated carbon, white clay and adsorbent resin.

The coenzyme Q10 crude product obtained in the above step 2) can be subjected to further purification treatment such as silica gel column chromatography, thereby obtaining high-purity coenzyme Q10.

In the present disclosure, the coenzyme Q10 fermentation bacterium powder refers to dried bacteria obtained by drying a coenzyme Q10 production strain after fermentation.

The coenzyme Q10 production bacterium may be a microorganism belonging to *Agrobacterium, Aspergillus, Acetobacter, Aminobacter, Agromonas ohta* and *Hattori, Acidiphilium, Bulleromyces, Bullera, Brevundimonas, Cryptococcus, Chionosphaera, Candida, Cerinosterus, Exisophiala, Exobasidium, Fellomyces, Filobasidiella, Filobasidium, Geotrichum, Graphiolaceae, Gluconobacter, Kockovaella, Kurtzmanomyces, Lalaria, Leucosporidium, Legionella, Methylobacterium, Mycoplana, Oosporidium, Pseudomonas, Psedozyma, Paracoccus, Petromyces, Rhodotorula, Red teliosporeae, Rhizomonas, Rhodobium, Rhodoplanes, Rhodopseudomonas, Rhodobacter, Sporobolomyces, Sporidiobolus, Saitoella, Shizosaccharomyces, Sphingomonas, Sporothrix, Sympodiomycopsis, Sterigmatosporidium, Taphrina, Tremella, Trichosporon, Tilletiaria, Tilletia, Tolyposporium, Tilletiopsis, Ustilago, Udeniomyces, Xanthophilomyces, Xanthobacter, Paecilomyces, Acremonium, Hyphomonas* or *Rhizobium.*

Preferably, the coenzyme Q10 production microorganism is *Rhodobacter sphaeroides*; more preferably, the *Rhodobacter sphaeroides* is a *Rhodobacter sphaeroides* strain with the accession number of deposit CGMCC No. 5997, a *Rhodobacter sphaeroides* strain with the accession number of deposit CGMCC No. 5998, and/or a *Rhodobacter sphaeroides* strain with the accession number of deposit CGMCC No. 5999.

As for the fermentation method of the coenzyme Q10 production microorganism, which can be referred to the prior art, such as the fermentation techniques in patent literature JP2008253271(A), CN105420417A, etc. Preferably, the on-line control of oxygen consumption rate and conductivity with reference to CN105420417A is combined with the technical solution of the present disclosure to carry out fermentation. Specifically, in the fermentation growth stage of *Rhodobacter sphaeroides*, the oxygen consumption rate is controlled to be between 30 and 150 mmol/(L·h) and the conductivity is stabilized between 5 and 30.0 ms/cm; in the synthesis and accumulation stage of the substrate, the oxygen consumption rate is controlled between 60 and 120 mmol/(L·h) and the conductivity is stabilized between 8 and 15.0 ms/cm. In the fermentation stage, the medium used is a conventional medium in the art which contains a carbon source, a nitrogen source, a phosphorus source, and a micronutrient. For example, 8 g of yeast powder, 3 g of ammonium chloride, 2.8 g of sodium chloride, 0.005 g of ferric citrate, 0.6 g of potassium dihydrogen phosphate, 0.9 g of dipotassium hydrogen phosphate, 12.55 g of magnesium sulfate, 0.1 g of calcium chloride are contained per liter of the medium; and the pH value is 7.0. The conductivity is controlled by a feed medium. The feed medium used in the present disclosure is not particularly limited, and may be any conventional medium containing a carbon source, a nitrogen source, a phosphorus source, and a micronutrient. For example, the feed medium has the following formula: 8 to 12 g of yeast powder, 5 to 10 g of ammonium sulfate, 1 to 2 g of magnesium sulfate, 3 to 6 g of sodium chloride, 2 to 4 g of potassium dihydrogen phosphate, 2 to 4 g dipotassium hydrogen phosphate, 1 to 2 g of calcium chloride, and 0.013 to 0.025 g of biotin are contained per liter of the feed liquid; and the pH value is 7.0.

EXAMPLES

A fermentation bacterium powder was prepared with reference to the fermentation technique in patent CN105420417A. For the details, see the following:

Seed culture: A cultured slant was washed with sterile water to make a bacterial suspension of $10^8$ to $10^9$ cells per ml, 10 ml of the suspension was transferred to a seed bottle with a loading capacity of 500 ml/1000 ml, and culture was performed under the conditions of 30° C. and 180 to 250 rpm for 22 to 26 hours.

Fermentation culture: The seed solution obtained in the above step was inoculated into a 5 liter fermenter containing a fermentation medium, wherein the inoculation amount was 10%, the culture temperature was 29 to 33° C., and the pressure in the fermenter was 0.03 to 0.05 Mpa; after inoculation, the initial stirring speed was 500 rpm and the air flow rate was 9 L/min. After 24 hours, the rotation speed was adjusted to 600 rpm; the adding rate of the feed medium was controlled to maintain the conductivity of the fermentation liquid in the range of 10 to 20 ms/cm; during the whole process, the residual glucose in the fermenter was controlled to be between 0.5% and 2.0%; and the fermentation culture lasted for about 110 hours.

The strain used was a *Rhodobacter sphaeroides* strain with the accession number of deposit CGMCC No. 5999.

The fermentation medium contained per liter of the medium: 8 g of yeast powder, 3 g of ammonium chloride, 2.8 g of sodium chloride, 0.005 g of ferric citrate, 0.6 g of potassium dihydrogen phosphate, 0.9 g of dipotassium hydrogen phosphate, 12.55 g of magnesium sulfate, and 0.1 g of calcium chloride; the pH value was adjusted to 7.0.

The formula of the feed medium was that each liter of the feed liquid contained: 12 g of yeast powder, 10 g of ammonium sulfate, 2 g of magnesium sulfate, 6 g of sodium chloride, 4 g of potassium dihydrogen phosphate, 4 g of dipotassium hydrogen phosphate, 2 g of calcium chloride, and 0.025 g of biotin; the pH value was adjusted to 7.0; and the conductivity of the feed medium was 23.0 ms/cm.

After the completion of the fermentation, the fermentation liquid was filtered to obtain wet bacteria. Drying was carried out at 60° C. to obtain a dried fermentation bacterium powder.

The bacterium powder was detected by the external standard method using the liquid chromatography. As a result, the content of a phospholipid was 11.99% and the content of coenzyme Q10 was 2.83%.

Example 1

100 g of the above coenzyme Q10 fermentation bacterium powder was weighed, and 300 g of a tetrahydrofuran-methanol mixed solvent (the volume fraction of the tetrahydrofuran was 72%, the three-dimensional Hansen solubility parameter of the mixed solvent was 22.2 $(J/cm^3)^{1/2}$, and the hydrogen bonding solubility parameter thereof was 12.0 $(J/cm^3)^{1/2}$) was added thereto for carrying out immersion extraction, wherein the extraction was carried out at 10° C. for 3 times to obtain a extraction liquor. The extraction liquor was concentrated to dryness, and the mixed solvent was recovered. The concentrate was dissolved in 200 g of n-hexane, and the insoluble substances were removed by filtration. The solution was then concentrated to be 60 g and 300 g of acetone was added thereto. Stirring was performed at 50° C. for 2 hours, and then the solution was cooled to 0° C. The temperature was kept to 0° C. for crystallization for 2 hours, and then filtration was carried out to obtain a filter cake and a filtrate. The obtained filter cake was washed with a small amount of acetone, and dried to obtain 12.1 g of a phospholipid, of which the purity was 95.2%, the yield was 96.1%, and the main components were phosphatidylglycerol, diphosphatidylglycerol, phosphatidylethanolamine and lecithin. The $^{31}$P NMR spectrum of the phospholipid is shown in FIG. 1.

Figure 2:
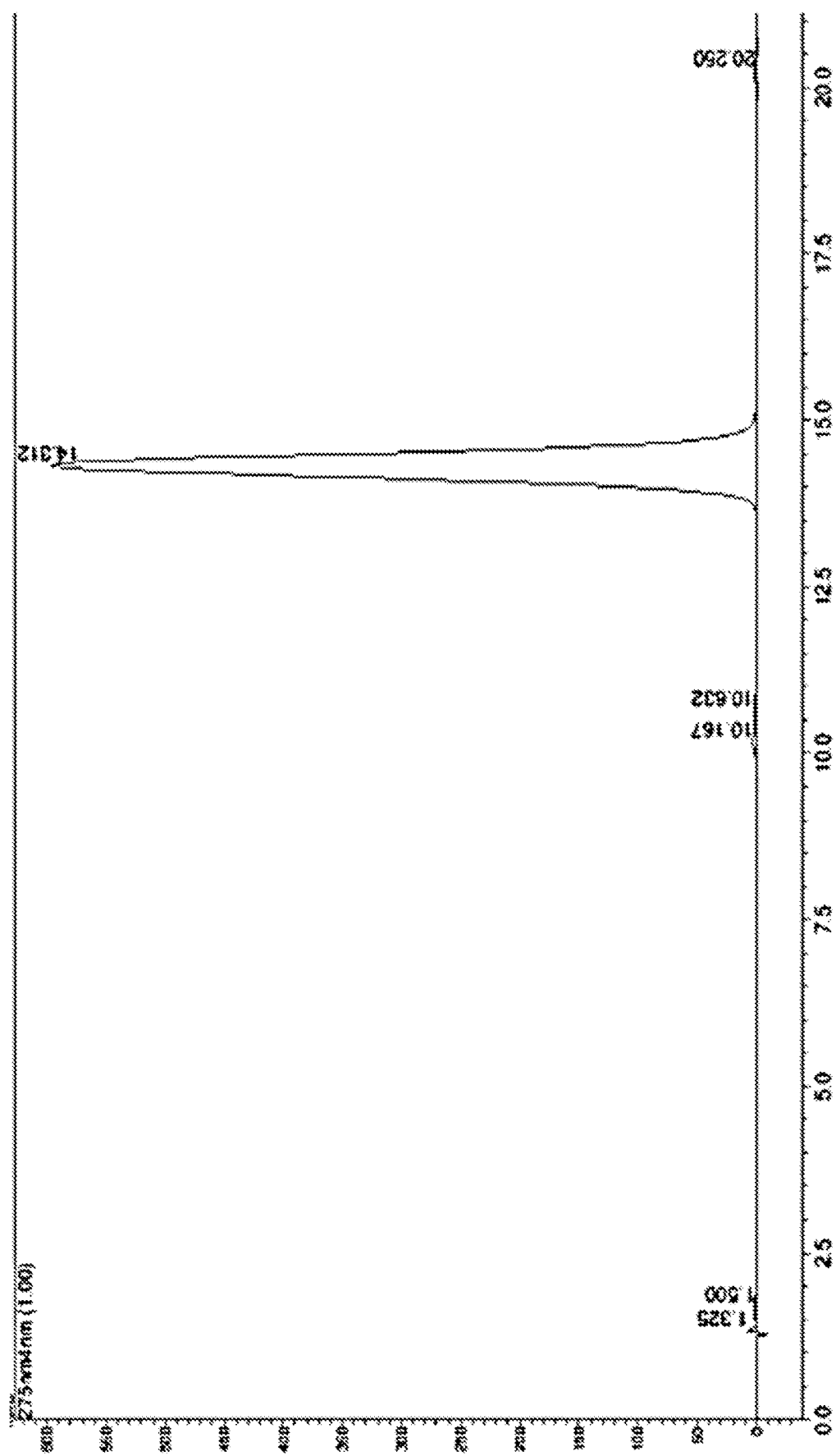
FIG. 2 is an HPLC chromatogram of the coenzyme Q10 product obtained in Example 1 as disclosed herein.

The filtrate and the acetone washing liquid above were combined and concentrated to dryness. 100 g of n-hexane was added thereto for dissolving, and then the solution was washed with 800 g of a methanol aqueous solution (the mass percentage of the methanol was 80%). The solution obtained after washing was concentrated to dryness. 40 g of ethanol was added thereto and dissolving was carried out with stirring at 60□. Activated carbon was added thereto to perform decolorization for 2 hours. The solution was filtered and the filtrate was cooled to 0° C. The temperature was kept to 0° C. for crystallization for 5 hours, and then filtration was carried out to obtain a coenzyme Q10 crude product. The coenzyme Q10 crude product was separated by silica gel column chromatography to obtain 2.72 g of a coenzyme Q10 product, of which the purity was 99.2% and the yield was 95.3%. The HPLC chromatogram is shown in FIG. 2.

Example 2

100 g of the above coenzyme Q10 fermentation bacterium powder was weighed, and 300 g of a tetrahydrofuran-methanol mixed solvent (the volume fraction of the tetrahydrofuran was 78%, the three-dimensional Hansen solubility parameter of the mixed solvent was 21.6 $(J/cm^3)^{1/2}$, and the hydrogen bonding solubility parameter thereof was 11.1 $(J/cm^3)^{1/2}$) was added thereto for carrying out immersion extraction, wherein the extraction was carried out at 10° C. for 5 times to obtain a extraction liquor. The extraction liquor was concentrated to dryness, and the mixed solvent was recovered. The concentrate was dissolved in 100 g of 2-methylpentane, and the insoluble substances were removed by filtration. The solution was then concentrated to be 30 g and 200 g of acetone was added thereto. Stirring was performed at 50° C. for 0.5 hour, and then the solution was cooled to 0° C. The temperature was kept to 0° C. for crystallization for 2 hours, and then filtration was carried out to obtain a filter cake and a filtrate. The obtained filter cake was washed with a small amount of acetone, and dried to obtain 11.9 g of a phospholipid, of which the purity was 96.5%, the yield was 95.8%, and the main components were phosphatidylglycerol, diphosphatidylglycerol, phosphatidylethanolamine and lecithin.

The filtrate and the acetone washing liquid above were combined and concentrated to dryness. 50 g of n-hexane was added thereto for dissolving, and then the solution was washed with 400 g of a methanol aqueous solution (the mass percentage of the methanol was 95%). The solution obtained after washing was concentrated to dryness. 30 g of ethanol was added thereto and dissolving was carried out with stirring at 50□. Activated carbon was added thereto to perform decolorization for 1 hour. The solution was filtered and the filtrate was cooled to 0° C. The temperature was kept to 0° C. for crystallization for 1 hour, and then filtration was carried out to obtain a coenzyme Q10 crude product. The coenzyme Q10 crude product was separated by silica gel column chromatography to obtain 2.76 g of a coenzyme Q10 product, of which the purity was 99.1% and the yield was 96.6%.

Example 2

100 g of the above coenzyme Q10 fermentation bacterium powder was weighed, and 800 g of a tetrahydrofuran-methanol mixed solvent (the volume fraction of the tetrahydrofuran was 84%, the three-dimensional Hansen solubility parameter of the mixed solvent was 21.0 $(J/cm^3)^{1/2}$, and the hydrogen bonding solubility parameter thereof was 10.3 $(J/cm^3)^{1/2}$) was added thereto for carrying out immersion extraction, wherein the extraction was carried out at 30□ twice to obtain a extraction liquor. The extraction liquor was concentrated to dryness, and the mixed solvent was recovered. The concentrate was dissolved in 300 g of n-pentane, and the insoluble substances were removed by filtration. The solution was then concentrated to be 40 g and 300 g of acetone was added thereto. Stirring was performed at 40□ for 1 hour, and then the solution was cooled to −10□.

The temperature was kept to −10° C. for crystallization for 0.5 hour, and then filtration was carried out to obtain a filter cake and a filtrate. The obtained filter cake was washed with a small amount of acetone, and dried to obtain 12.3 g of a phospholipid, of which the purity was 95.1%, the yield was 97.6%, and the main components were phosphatidylglycerol, diphosphatidylglycerol, phosphatidylethanolamine and lecithin.

The filtrate and the acetone washing liquid above were combined and concentrated to dryness. 200 g of n-hexane was added thereto for dissolving, and then the solution was washed with 400 g of an ethanol aqueous solution (the mass percentage of the ethanol was 60%). The solution obtained after washing was concentrated to dryness. 20 g of ethanol was added thereto and dissolving was carried out with stirring at 40□. An adsorbent resin was added thereto to perform decolorization for 2 hours. The solution was filtered and the filtrate was cooled to 10° C. The temperature was kept to 10° C. for crystallization for 4 hours, and then filtration was carried out to obtain a coenzyme Q10 crude product. The coenzyme Q10 crude product was separated by silica gel column chromatography to obtain 2.72 g of a coenzyme Q10 product, of which the purity was 99.5% and the yield was 95.6%.

Example 4

100 g of the above coenzyme Q10 fermentation bacterium powder was weighed, and 500 g of a chloroform-ethanol mixed solvent (the volume fraction of the chloroform was 54%, the three-dimensional Hansen solubility parameter of the mixed solvent was 22.5 $(J/cm^3)^{1/2}$, and the hydrogen bonding solubility parameter thereof was 12.0 $(J/cm^3)^{1/2}$) was added thereto for carrying out reflux extraction, wherein the extraction was carried out at 60□ twice to obtain a extraction liquor. The extraction liquor was concentrated to dryness, and the mixed solvent was recovered. The concentrate was dissolved in 200 g of isopentane, and the insoluble substances were removed by filtration. The solution was then concentrated to be 40 g and 400 g of acetone was added thereto. Stirring was performed at 30□ for 2 hours, and then the solution was cooled to −10□. The temperature was kept to −10° C. for crystallization for 2 hours, and then filtration was carried out to obtain a filter cake and a filtrate. The obtained filter cake was washed with a small amount of acetone, and dried to obtain 12.0 g of a phospholipid, of which the purity was 95.8%, the yield was 95.9%, and the main components were phosphatidylglycerol, diphosphatidylglycerol, phosphatidylethanolamine and lecithin.

The filtrate and the acetone washing liquid above were combined and concentrated to dryness. 100 g of n-hexane was added thereto for dissolving, and then the solution was washed with 100 g of an ethanol aqueous solution (the mass percentage of the ethanol was 85%). The solution obtained after washing was concentrated to dryness. 50 g of ethanol was added thereto and dissolving was carried out with stirring at 60□. Activated carbon was added thereto to perform decolorization for 2 hours and the solution was then cooled to 10° C. The temperature was kept to 10° C. for crystallization for 6 hours, and then filtration was carried out to obtain a coenzyme Q10 crude product. The coenzyme Q10 crude product was separated by silica gel column chromatography to obtain 2.75 g of a coenzyme Q10 product, of which the purity was 99.1% and the yield was 96.3%.

Example 5

100 g of the above coenzyme Q10 fermentation bacterium powder was weighed, and 1000 g of an n-hexane-n-propanol mixed solvent (the volume fraction of the n-hexane was 35%, the three-dimensional Hansen solubility parameter of the mixed solvent was 21.1 $(J/cm^3)^{1/2}$, and the hydrogen bonding solubility parameter thereof was 11.3 $(J/cm^3)^{1/2}$) was used in a percolator to carry out percolation extraction, wherein the extraction was carried out at 20□ for 3 times to obtain a extraction liquor. The extraction liquor was concentrated to dryness, and the mixed solvent was recovered. The concentrate was dissolved in 500 g of petroleum ether, and the insoluble substances were removed by filtration. The solution was then concentrated to be 80 g and 600 g of acetone was added thereto. Stirring was performed at 30□ for 2 hours, and then the solution was cool to 10□. The temperature was kept to 10° C. for crystallization for 3 hours, and then filtration was carried out to obtain a filter cake and a filtrate. The obtained filter cake was washed with a small amount of acetone, and dried to obtain 11.8 g of a phospholipid, of which the purity was 97.1%, the yield was 95.6%, and the main components were phosphatidylglycerol, diphosphatidylglycerol, phosphatidylethanolamine and lecithin.

The filtrate and the acetone washing liquid above were combined and concentrated to dryness. 300 g of n-hexane was added thereto for dissolving, and then the solution was washed with 200 g of an isopropanol aqueous solution (the mass percentage of the isopropanol was 50%). The solution obtained after washing was concentrated to dryness. 60 g of ethanol was added thereto and dissolving was carried out with stirring at 50□ for 3 hours. Activated carbon was added thereto to perform decolorization for 3 hours. The solution was filtered and the filtrate was cooled to 20° C. The temperature was kept to 20° C. for crystallization for 5 hours, and filtration was carried out to obtain a coenzyme Q10 crude product. The coenzyme Q10 crude product was separated by silica gel column chromatography to obtain 2.77 g of a coenzyme Q10 product, of which the purity was 99.4% and the yield was 97.3%.

Example 6

100 g of the above coenzyme Q10 fermentation bacterium powder was weighed, and 400 g of an ethyl acetate-ethanol mixed solvent (the volume fraction of the ethyl acetate was 61%, the three-dimensional Hansen solubility parameter of the mixed solvent was 21.4 $(J/cm^3)^{1/2}$, and the hydrogen bonding solubility parameter thereof was 12.0 $(J/cm^3)^{1/2}$) was added thereto for carrying out immersion extraction, wherein the extraction was carried out at 60□ twice to obtain a extraction liquor. The extraction liquor was concentrated to dryness, and the mixed solvent was recovered. The concentrate was dissolved in 200 g of petroleum ether, and the insoluble substances were removed by filtration. The solution was then concentrated to be 90 g and 800 g of acetone was added thereto. Stirring was performed at 20□ for 3 hours, and then the solution was cool to 10□. The temperature was kept to 10° C. for crystallization for 5 hours, and then filtration was carried out to obtain a filter cake and a filtrate. The obtained filter cake was washed with a small amount of acetone, and dried to obtain 12.0 g of a phospholipid, of which the purity was 96.4%, the yield was 96.5%, and the main components were phosphatidylglycerol, diphosphatidylglycerol, phosphatidylethanolamine and lecithin.

The filtrate and the acetone washing liquid above were combined and concentrated to dryness. 400 g of n-hexane was added thereto for dissolving, and then the solution was washed with 200 g of an isopropanol aqueous solution (the mass percentage of the isopropanol was 70%). The solution obtained after washing was concentrated to dryness. 80 g of ethanol was added thereto and dissolving was carried out with stirring at 70□. White clay was added thereto to perform decolorization for 0.5 hour. The solution was filtered and the filtrate was cooled to 20° C. The temperature was kept to 20° C. for crystallization for 10 hours, and then filtration was carried out. The filter cake was added into 40 g of ethanol for recrystallization, thereby obtaining a coenzyme Q10 crude product. The coenzyme Q10 crude product was separated by silica gel column chromatography to obtain 2.70 g of a coenzyme Q10 product, of which the purity was 99.6% and the yield was 95.0%.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A method for extracting coenzyme Q10 and a phospholipid from a coenzyme Q10 fermentation bacterium powder, wherein a fermentation bacterium powder of a coenzyme Q10 production strain is subjected to extraction with a mixed solvent of which a three-dimensional Hansen solubility parameter is between 21 and 23 $(J/cm^3)^{1/2}$ and a hydrogen bonding solubility parameter thereof is between 10 and 12 $(J/cm^3)^{1/2}$, wherein an extraction liquor obtained after carrying out the extraction is subjected to separation by the following method, in said method,
   1) the extraction liquor is concentrated to dryness, the resultant is dissolved with a low-polarity solvent, filtered to remove insoluble substances, concentrated again to a weight which is 30% to 90% of the weight of the coenzyme Q10 fermentation bacterium powder, and then added into acetone; after being completely mixed and dissolved, the resultant is subjected to cooling and crystallization, and filtered to obtain a filter cake and a filtrate; the filter cake is washed with acetone, and a phospholipid is obtained after drying; and
   2) the filtrate and a washing liquid obtained in step 1) are combined, the resultant is concentrated to dryness, n-hexane is added thereto for dissolving, and then the resultant is washed with a lower alcohol aqueous solution; and the solution obtained after washing is concentrated to dryness, ethanol is added thereto for dissolving, and then the resultant is subjected to cooling and crystallization to obtain a coenzyme Q10 crude product.

2. The method according to claim 1, wherein the coenzyme Q10 and the phospholipid are both extracted from the coenzyme Q10 fermentation bacterium powder by contact with the mixed solvent having the Hansen solubility parameter and the hydrogen bonding solubility parameter as defined.

3. The method according to claim 1, wherein the mixed solvent is a mixed solvent formed by a solvent (a) and a solvent (b), the solvent (a) is at least one of tetrahydrofuran, ethyl acetate, diethyl ether, butanone, dichloromethane, chloroform, n-pentane, n-hexane, n-heptane and cyclohexane, and the solvent (b) is at least one of methanol, ethanol, n-propanol and isopropanol.

4. The method according to claim 3, wherein the mixed solvent is tetrahydrofuran-methanol, ethyl acetate-methanol, ethyl acetate-ethanol, chloroform-methanol, chloroform-ethanol, n-hexane-methanol, n-hexane-ethanol, or n-hexane-n-propanol.

5. The method according to claim 1, wherein a using amount of the mixed solvent is 3 to 10 times the weight of the coenzyme Q10 fermentation bacterium powder.

6. The method according to claim 1, wherein the extraction is one of immersion extraction, percolation extraction, reflux extraction, decoction extraction and ultrasonic-assisted extraction.

7. The method according to claim 1, wherein the low-polarity solvent in the step 1) is one of pentane, hexane and petroleum ether.

8. The method according to claim 1, wherein the using amount of acetone used in the step 1) is 2 to 8 times the weight of the coenzyme Q10 fermentation bacterium powder; and the using amount of n-hexane used in step 2) is 0.5 to 4 times the weight of the coenzyme Q10 fermentation bacterium powder.

9. The method according to claim 1, wherein the lower alcohol aqueous solution in the step 2) is one of methanol aqueous solution, ethanol aqueous solution and isopropanol aqueous solution.

10. The method according to claim 1, wherein a temperature for the crystallization in the step 2) is 0 to 20° C.

11. The method according to claim 1, wherein in the step 2), a decolorizing agent is added before crystallization to perform a decolorizing treatment.

12. The method according to claim 1, wherein the coenzyme Q10 crude product obtained in the step 2) is subjected to silica gel column chromatography to obtain a high-purity coenzyme Q10.

13. The method according to claim 5, wherein a temperature of the extraction is 10 to 60° C., and the extraction is carried out 2 to 5 times.

14. The method according to claim 6, wherein the extraction is the immersion extraction.

15. The method according to claim 7, wherein a using amount of the low-polarity solvent is 1 to 5 times the weight of the coenzyme Q10 fermentation bacterium powder.

16. The method according to claim 9, wherein the lower alcohol therein has a mass percentage of 50% to 95%.

17. The method according to claim 9, wherein the using amount of the lower alcohol aqueous solution is 1 to 8 times the weight of the coenzyme Q10 fermentation bacterium powder.

18. The method according to claim 10, wherein the using amount of ethanol is 0.2 to 0.8 times the weight of the coenzyme Q10 fermentation bacterium powder.

19. The method according to claim 11, wherein the decolorizing agent is one of activated carbon, white clay, and adsorbent resin.

20. The method according to claim 1, wherein the coenzyme Q10 and the phospholipid are both extracted from the coenzyme Q10 fermentation bacterium powder, and wherein the mixed solvent is present in an amount 3 to 10 times the weight of the coenzyme Q10 fermentation bacterium powder.

* * * * *